US00PP14259P29

(12) United States Plant Patent
Hanes

(10) Patent No.: US PP14,259 P2
(45) Date of Patent: Oct. 28, 2003

(54) GERANIUM PLANT NAMED 'FREE BURG TWO'

(50) Latin Name: *Pelargonium peltatum*
Varietal Denomination: Free Burg Two

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/400,057

(22) Filed: Mar. 25, 2003

(51) Int. Cl.[7] ..... A01H 5/00
(52) U.S. Cl. ..... Plt./332
(58) Field of Search ..... Plt./332

*Primary Examiner*—Kent Bell
(74) *Attorney, Agent, or Firm*—Jondle & Associates, PC

(57) ABSTRACT

A geranium cultivar particularly distinguished by dark green foliage with light zonation, burgundy flower color, and semi-double flowers on large umbels, fast rooting and exhibits vigorous growth.

1 Drawing Sheet

Genus and species: *Pelargonium peltatum.*
Variety denomination: 'Free Burg Two'.

BACKGROUND OF THE NEW PLANT

The present invention comprises a new and distinct cultivar of geranium, botanically known as *Pelargonium peltatum,* and hereinafter referred to by the cultivar name 'Free Burg Two'. The new cultivar originated from the cross of patented seed parent known as 'Freestyle Burgundy', a patented (U.S. Plant Pat. No. 12,580)×'Taj Mahal', a patented (U.S. Plant Pat. No. 12,228) line.

'Free Burg Two' is a product of a planned breeding program intended to create new geranium cultivars with burgundy colored flowers, semi-double flower form, green foliage, vigorous growth and superior cutting productivity.

The new cultivar was created in 2000 in Gilroy, Calif. and has been repeatedly asexually reproduced by cuttings in Gilroy, Calif., Guatemala and Kenya over a two and half-year period. It has also been trialed at Gilroy, Calif., Litchfield, Mich. and Andijk, The Netherlands. It has been found to retain its distinctive characteristics through successive asexual propagations; and this novelty is firmly fixed.

DESCRIPTION OF PHOTOGRAPH

This new geranium plant is illustrated by the accompanying photograph which shows blooms, buds, and foliage of the plant in full color, the colors shown being as true as can be reasonably obtained by conventional photographic procedures.

The photograph shows umbels and flowers of 'Free Burg Two'.

DESCRIPTION OF THE NEW CULTIVAR

The following detailed descriptions set forth the distinctive characteristics of 'Free Burg Two'. The data which defines these characteristics were collected from asexual reproductions carried out in Gilroy, Calif. The plant history was taken on 10 month old plants blossomed in one-gallon pots in the fall/winter season, in poly-covered greenhouse under natural light in a greenhouse and color readings were taken in the greenhouse in Gilroy, Calif. under natural light.

Plants had been cut back numerous times prior to data readings taken. Color references are primarily to the R.H.S. Colour Chart of The Royal Horticultural Society of London (R.H.S.). Texture description details were observed under a dissecting microscope.

DETAILED BOTANICAL DESCRIPTION

Classification:
*Botanical.*—*Pelargonium peltatum.*
*Commercial.*—Ivy Geranium.
Form: Semi upright and decumbent.
Growth and branching habit: Good vigorous habit, well branched.
Height: From soil level to top of plant (excluding blooms) 13–18 cm; from soil level to top of umbels 15–20 cm.
Width: 50–60 cm if lateral branches are outstretched the width is approximately 140 cm.
Time to produce a finished flowering plant: 8–14 weeks for 4–6 inch pots.
Outdoor plant performance: Good heat tolerance, used in hanging baskets, patio or mixed containers.
Time to initiate roots: 10–28 days.
Root description: White, slightly pubescent, fibrous yet coarse.

The Leaves

Color: Upper side, darker green than RHS 146A (yellow-green); Underside, between RHS 146A and B (yellow-green) and ribs between RHS 144A/B (yellow-green).
Length: 9–10.5 cm.
Width: 8–8.5 cm.
Apex description: Mucronulate-Cuspidate.
Base description: Cordate.
Shape: Reniform.
Margin: Entire- Ciliate.
Texture: Short glandular hairs.
Zonation color: RHS 200A (brown).
Zonation diameter: 3.3 cm.
Venation type: Palmate.
Venation color: Between RHS 146C and D (yellow-green).
Petiole color: RHS 144A (yellow-green).
Petiole length: 5.0–5.8 cm.

Petiole diameter: 0.25 cm.
Petiole texture: Villous, short glandular hairs.

The Stem

Color: RHS 144A (yellow-green).
Length: 50–70 cm.
Internode length: 5.0–6.0 cm.
Texture: Strigulose and some short glandular hairs.

The Bud

Diameter: 0.9–1.1 cm.
Length: 1.3–1.5 cm.
Shape: Elliptic-Oval.
Color when sepals first divide: RHS 187C (greyed-purple).

The Inflorescence

Peduncle color: RHS 144A (yellow-green).
Peduncle length: 9.5–20 cm.
Peduncle diameter: 0.25–0.4 cm.
Peduncle texture: Strigulose.
Pedicel color: RHS 144A (yellow-green) with some reddish anthocyanin.
Pedicle length: 2.7–3.0 cm.
Pedicel diameter: 0.2–0.3 cm.
Pedicel texture: Pilose, widely scattered.

The Flower

Type: An umbel composed of approximately 5–10 flowers.
Blooming habit: Continuous blooming throughout the growing season. Good floriferousness.
Diameter: 8.0–10.0 cm.
Depth: 5.0–7.5 cm.
Floret form: Polypetalous; 11–14 cm mostly imbricate petals, 3–5 petaloids.
Upper petal color: Closest to RHS 61A (red-purple), but more velvety red and RHS 59A (red-purple) macure; Undersurface, close to RHS 61B (red-purple) with streaks of RHS 59C (red-purple).
Upper petaloid color: Closest to RHS 61A (red-purple).
Lower petal color: Closest to RHS 61A (red-purple); Undersurface, close to RHS 59A (red-purple).
Lower petaloid color: Closest to RHS 61A (red-purple).
Color change with age: Colors do not change with age but may change with temperature and time of year.
Floret diameter: 5.0–6.0 cm.
Petal shape: Spathulate.
Petal apex shape: Rounded.
Petal base shape: Acuminate.
Petal margin: Entire.
Petal texture: Papillose.
Flower persistence: An open flower will hold its petals until the flower begins to dehisce or approximately 7–10 days.
Fragrance: None.
Number of sepals: 5, 1 larger than the other, fused at base.
Sepal color: RHS 144B (yellow-green) with slight RHS N155B (white) margin.
Sepal length: 1.6–1.8 cm.
Sepal width: 0.5–0.65 cm.
Sepal shape: Linear-Lanceolate.
Sepal apex shape: Aristate.
Sepal texture: Villous, short glandular hairs, and hirsute mainly on the white margin.

The Reproductive Organs

Stamens: 4–6.
Filament color: White basally, RHS 63B (red-purple) apically.
Pollen color: RHS N 172A (greyed-orange).
Pistil: 1.
Stigma color: RHS 59B (red-purple).
Style color: White.
Fruit set: Not observed.

Disease and Insect Resistance

Less susceptibility to Oedema.

Comparison with Known Cultivars

'Free Burg Two' differs from the female parent in the following ways: The female is slower growing and is slightly earlier to flower than 'Free Burg Two'.

'Free Burg Two' differs from the male parent in the following ways: 'Taj Mahal' is less vigorous and has a burgundy with a bluer tint than 'Free Burg Two'.

I claim:

1. A new and distinct cultivar of geranium plant as shown and described herein.

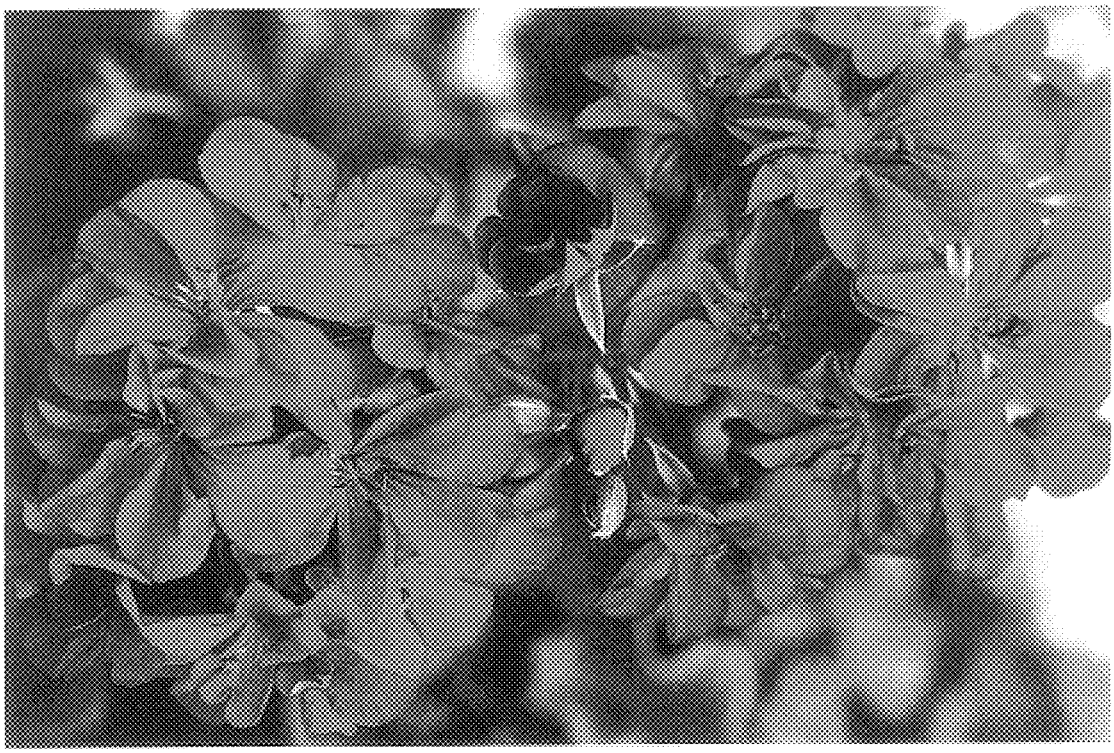

* * * * *